United States Patent
Koseoglu et al.

(10) Patent No.: US 11,261,386 B2
(45) Date of Patent: Mar. 1, 2022

(54) CONVERSION OF MEROX PROCESS BY-PRODUCTS TO USEFUL PRODUCTS IN AN INTEGRATED REFINERY PROCESS

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/878,939

(22) Filed: May 20, 2020

(65) Prior Publication Data
US 2021/0363437 A1    Nov. 25, 2021

(51) Int. Cl.
*C07C 7/10* (2006.01)
*C10G 55/04* (2006.01)
(Continued)

(52) U.S. Cl.
CPC ............... *C10G 55/04* (2013.01); *C07C 4/04* (2013.01); *C07C 7/005* (2013.01); *C07C 7/10* (2013.01);
(Continued)

(58) Field of Classification Search
None
See application file for complete search history.

(56) References Cited

U.S. PATENT DOCUMENTS 4,081,354 A * 3/1978 Christman ........... B01D 11/043 208/206
9,580,661 B2 2/2017 Koseoglu
(Continued)

FOREIGN PATENT DOCUMENTS

EP    1176186 A2    1/2002
EP    2103669 A2    9/2009
(Continued)

OTHER PUBLICATIONS

Viennet et al., "The Influence of Dimethyl Disulfide on Naphtha Steam Cracking", Industrial & Engineering Chemistry Research, 2001, 40(20), 4353-4362. (Year: 2001).*
Petroleum HPV Testing Group, "U.S. EPA HPV Challenge Program—Data Review and Assessment for Reclaimed Substances: Disulfides, Diethyl and Diphenyl, Naphtha Sweetening (Revised) (aka Disulfide Oil)", 2010, pp. 1-51 (Year: 2010).*
(Continued)

*Primary Examiner* — Philip Y Louie
(74) *Attorney, Agent, or Firm* — Dinsmore & Shohl LLP

(57) ABSTRACT

An integrated refinery process for removing mercaptans from a hydrocarbon stream containing mercaptans and converting by-product disulfide oil to useful products. The process includes introducing the hydrocarbon stream containing mercaptans into an extraction vessel containing an alkaline solution and passing the hydrocarbon stream through an extraction section of the extraction vessel which includes one or more liquid-liquid contacting decks for reaction to convert the mercaptans to alkali metal alkanethiolates. Further, the process includes withdrawing a hydrocarbon product stream free of mercaptans from the extraction vessel and recovering spent caustic containing alkali metal alkanethiolates from the extraction vessel. Additionally, the process includes subjecting the spent caustic containing alkali metal alkanethiolates to air oxidation to produce a by-product stream containing disulfide oils (DSO) and sulfides and processing the by-product stream in a steam cracking unit to produce a DSO free product stream.

9 Claims, 3 Drawing Sheets

(51) Int. Cl.
*C07C 7/148* (2006.01)
*C07C 7/00* (2006.01)
*C07C 4/04* (2006.01)
*C10L 3/10* (2006.01)
*C10L 3/12* (2006.01)
*C10L 1/06* (2006.01)
*C10L 1/08* (2006.01)

(52) U.S. Cl.
CPC ............ *C07C 7/14816* (2013.01); *C10L 1/06* (2013.01); *C10L 1/08* (2013.01); *C10L 3/103* (2013.01); *C10L 3/12* (2013.01); *C10G 2300/104* (2013.01); *C10G 2300/1025* (2013.01); *C10G 2300/1044* (2013.01); *C10G 2300/1051* (2013.01); *C10G 2300/1055* (2013.01); *C10G 2300/202* (2013.01); *C10G 2300/207* (2013.01); *C10G 2400/02* (2013.01); *C10G 2400/04* (2013.01); *C10G 2400/08* (2013.01); *C10G 2400/26* (2013.01); *C10G 2400/30* (2013.01); *C10L 2200/043* (2013.01); *C10L 2200/0423* (2013.01); *C10L 2200/0446* (2013.01); *C10L 2270/023* (2013.01); *C10L 2270/026* (2013.01); *C10L 2270/04* (2013.01); *C10L 2290/544* (2013.01)

(56) References Cited

U.S. PATENT DOCUMENTS

| | | |
|---|---|---|
| 9,598,647 B2 | 3/2017 | Bourane et al. |
| 10,240,096 B1 | 3/2019 | Koseoglu et al. |
| 2018/0282632 A1* | 10/2018 | Hakola ................. C10G 69/126 |
| 2018/0320089 A1* | 11/2018 | Besnault ................ C10G 53/12 |

FOREIGN PATENT DOCUMENTS

| | | |
|---|---|---|
| WO | 0196499 A1 | 12/2001 |
| WO | 2005111175 A1 | 11/2005 |
| WO | 2007074127 A1 | 7/2007 |

OTHER PUBLICATIONS

International Search Report and Written Opinion dated Feb. 10, 2021 pertaining to International application No. PCT/US2020/055239 filed Oct. 12, 2020, 14 pgs.

* cited by examiner

CONVERSION OF MEROX PROCESS BY-PRODUCTS TO USEFUL PRODUCTS IN AN INTEGRATED REFINERY PROCESS

TECHNICAL FIELD

The present disclosure relates to an integrated refinery process for the treatment of the disulfide oil (DSO) compounds that are produced as a by-product of a mercaptan oxidation (MEROX) process.

BACKGROUND

The presence of mercaptans in petroleum products is generally considered undesirable as they possess an unpleasant odor and corrosively as well as degrade the stability of end-product fuels. Processes in oil refineries and natural gas processing plants that remove mercaptans are commonly referred to as sweetening processes because they result in products which no longer poses the sour, foul odors of mercaptans.

One process which has previously been utilized in the sweetening processes for the removal of mercaptans from any of a variety of petroleum streams including liquefied petroleum gas, naphtha, and other hydrocarbon fractions is a mercaptans oxidation process (MEROX). However, disulfide oil (DSO) compounds are produced as a by-product of the MEROX process in which the mercaptans are removed from any of the petroleum streams. Because of regulatory requirements to reduce the sulfur content of fuels for environmental reasons, refineries have been, and continue to be faced with the disposal of large volumes of sulfur-containing by-products including DSO from the MEROX process.

The DSO produced by the MEROX unit can be processed or disposed of in various other refinery units operations, but each previous attempt presents a major drawback. For example, the DSO may be added to the fuel oil pool at the expense of a resulting higher sulfur content of the fuel oil pool. The DSO has also previously been processed in a hydrotreating/hydrocracking unit at the expense of higher hydrogen consumption. Further, while the vapor pressure of disulfides are relatively low compared to those of mercaptans, so that their presence is less objectionable from the standpoint of odor, they are not environmentally acceptable due to their sulfur content making their disposal problematic.

SUMMARY

Accordingly, there is a clear and long-standing need to provide an efficient and economical process for the environmentally acceptable disposal and utilization of the large volumes of DSO by-products to thereby enhance the value of this class of by-products to the refiner.

In accordance with one or more embodiments of the present disclosure, an integrated refinery process for removing mercaptans from a hydrocarbon stream containing mercaptans and converting by-product disulfide oil to useful products is disclosed. The process includes (i) introducing the hydrocarbon stream containing mercaptans into an extraction vessel containing an alkaline solution; (ii) passing the hydrocarbon stream through an extraction section of the extraction vessel which includes one or more liquid-liquid contacting decks for reaction to convert the mercaptans to alkali metal alkanethiolates; (iii) withdrawing a hydrocarbon product stream free of mercaptans from the extraction vessel; (iv) recovering spent caustic containing alkali metal alkanethiolates from the extraction vessel; (v) subjecting the spent caustic containing alkali metal alkanethiolates to air oxidation to produce a by-product stream containing disulfide oils (DSO) and sulfides; and (vi) processing the by-product stream in a steam cracking unit to produce a DSO free product stream.

In accordance with one or more embodiments of the present disclosure, an integrated refinery process for removing mercaptans from a hydrocarbon stream containing mercaptans and converting by-product disulfide oil to useful products is disclosed. The process includes (i) introducing the hydrocarbon stream containing mercaptans into an extraction vessel containing an alkaline solution; (ii) passing the hydrocarbon stream through an extraction section of the extraction vessel which includes one or more liquid-liquid contacting decks for reaction to convert the mercaptans to alkali metal alkanethiolates; (iii) withdrawing a hydrocarbon product stream free of mercaptans from the extraction vessel; (iv) recovering spent caustic containing alkali metal alkanethiolates from the extraction vessel; (v) subjecting the spent caustic containing alkali metal alkanethiolates to air oxidation to produce a by-product stream containing disulfide oils (DSO) and sulfides; (vi) combining the by-product stream with one or more hydrocarbon streams; and (vii) processing the by-product stream in a steam cracking unit to produce a DSO free product stream.

Throughout the present disclosure, the terms "disulfide oil(s)", "disulfide compound(s)", "DSO", "DSO mixture", "DSO composition", and "DSO compound(s)" may be used interchangeably for convenience.

Additional features and advantages of the described embodiments will be set forth in the detailed description that follows. The additional features and advantages of the described embodiments will be, in part, readily apparent to those skilled in the art from that description or recognized by practicing the described embodiments, including the detailed description that follows as well as the drawings and the claims.

BRIEF DESCRIPTION OF THE DRAWINGS

The following detailed description of specific embodiments of the present disclosure can be best understood when read in conjunction with the following drawings in which.

FIGURE (FIG. 1 is a schematic illustration of a typical mercaptans oxidation (MEROX) process of the prior art.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Figure 1:
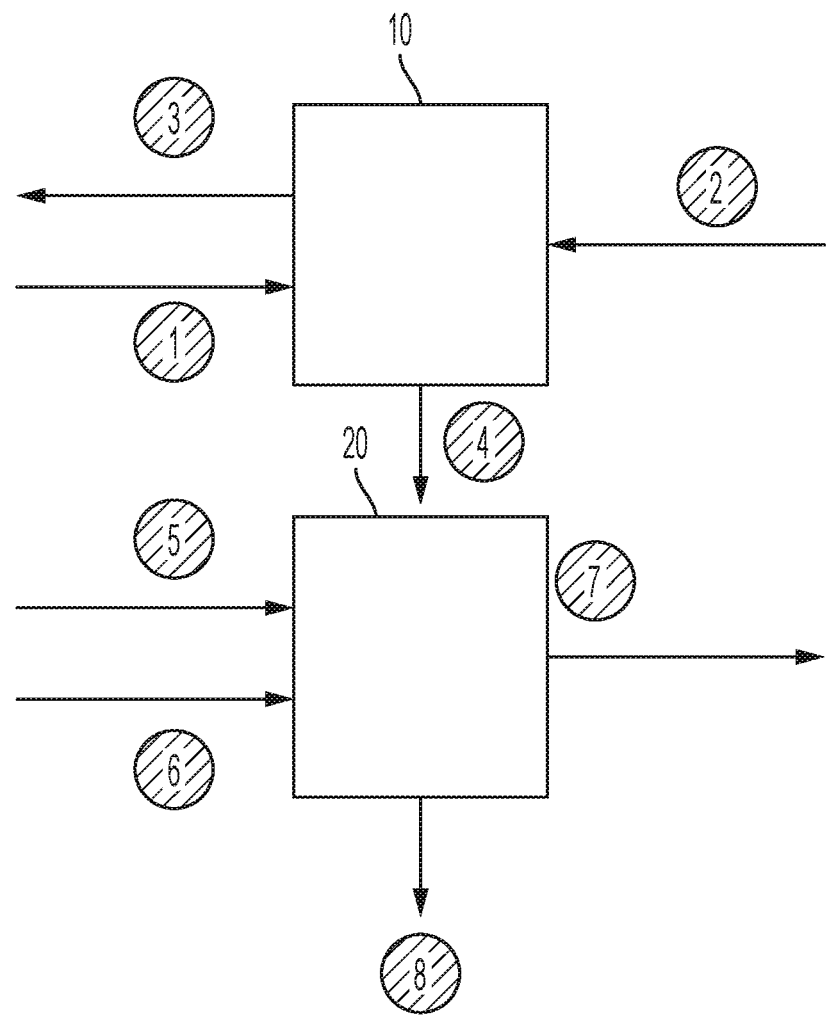

Embodiments of an integrated refinery process for removing mercaptans from a hydrocarbon stream containing mercaptans and converting by-product disulfide oil to useful products are provided in the present disclosure.

The MEROX process for removal of mercaptans from a hydrocarbon stream will now be presented in greater detail. Disulfide oil (DSO) compounds are produced as a by-product of the MEROX process. The term "DSO" is used for convenience in this description and in the claims, and will be understood to include the mixture of disulfide oils produced as by-products of the MEROX process.

The designation "MEROX" originates from the function of the process itself, that is the conversion of mercaptans by oxidation. The MEROX process in all of its applications is based on the ability of an organometallic catalyst in a basic environment, such as a caustic, to accelerate the oxidation of mercaptans to disulfides at near ambient temperatures and pressures. The overall reaction can be expressed as follows provided in Formula (1) as presented infra.

4RSH+O$_2$→2RSSR+2H$_2$O      Formula (1)

R represents a hydrocarbon chain that may be straight, branched, or cyclic, and the chains may be saturated or unsaturated. In most petroleum fractions, there is a mixture of mercaptans present such that the R may have 1, 2, 3, up to 10 or more carbon atoms in the chain. This variable chain length may be indicated by R and R' in the revised reaction provided as Formula (2).

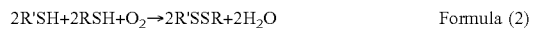
2R'SH+2RSH+O$_2$→2R'SSR+2H$_2$O      Formula (2)

The reactions in accordance with Formula (1) and Formula (2) may occur spontaneously, but at a very slow rate, whenever any sour mercaptan-bearing distillate is exposed to atmospheric oxygen. The reactions may be catalyzed in the presence of an alkali caustic solution, such as sodium hydroxide allowing the mercaptan oxidation to proceed at an economically practical rate at moderate refinery downstream temperatures.

The MEROX process can be conducted on both liquid streams and on combined gas and liquid streams. In the case of liquid streams, the mercaptans are converted directly to disulfides which remain in the product so that there is no reduction in total sulfur content of the effluent stream. The MEROX process typically utilizes a fixed bed reactor system for liquid streams and is normally employed with charge stocks having end points above 135° C. to 150° C. Mercaptans are converted to disulfides in the fixed bed reactor system over a catalyst, for example, an activated charcoal impregnated with the MEROX reagent, and wetted with caustic solution. Air is injected into the hydrocarbon feedstream ahead of the reactor and the mercaptans in the feed are oxidized to disulfides when passing through the catalyst-impregnated bed. The disulfides are substantially insoluble in the caustic and remain in the hydrocarbon phase. Post treatment is required to remove undesirable by-products resulting from known side reactions such as the neutralization of H$_2$S, the oxidation of phenolic compounds, entrained caustic, and others. In the case of mixed gas and liquid streams, extraction is applied to both phases of the hydrocarbon streams. The degree of completeness of the mercaptan extraction depends upon the solubility of the mercaptans in the alkaline solution, which is a function of the molecular weight of the individual mercaptans, the extent of the branching of the mercaptan molecules, the concentration of the caustic soda and the temperature of the system. Thereafter, the resulting DSO compounds are separated and the caustic solution is regenerated by oxidation with air in the presence of the catalyst and reused.

With reference to FIG. 1, a simplified schematic of a generalized conventional version of a MEROX process is provided. The MEROX process employs liquid-liquid extraction for removing sulfur compounds in which a mercaptan containing hydrocarbon stream 1 is treated. The example MEROX process of FIG. 1 includes the steps of introducing the hydrocarbon stream 1 with a homogeneous cobalt-based catalyst into an extraction vessel 10 containing a caustic solution 2; passing the hydrocarbon catalyst stream in counter-current flow through the extraction section of the extraction vessel 10 in which the extraction section includes one or more liquid-liquid contacting extraction decks or trays (not shown) for the catalyzed reaction with the circulating caustic solution to convert the mercaptans to water soluble alkali metal alkanethiolate compounds; withdrawing a hydrocarbon product stream 3 that is free or substantially free of mercaptans from the extraction vessel 10; recovering a combined spent caustic and alkali metal alkanethiolate stream 4 from the extraction vessel 10; subjecting the spent caustic to catalyzed wet air oxidation in a reactor 20 into which is introduced catalyst 5 and air 6 to provide the regenerated spent caustic 8 and convert the alkali metal alkanethiolate compounds to disulfide oils; and recovering a by-product stream 7 of disulfide oil (DSO) compounds and a minor proportion of other sulfides such as mono-sulfides and tri-sulfides.

The effluents of the wet air oxidation step in the MEROX process preferably comprise a minor proportion of sulfides and a major proportion of disulfide oils. It will be appreciated that in accordance with the reaction stoichiometry presented supra, sulfides represent less than 1 weight percent (wt. %) of the effluents. Further, as is known to those of skill in the art, the composition of this effluent stream depends on the effectiveness of the MEROX process, and sulfides are assumed to be carried-over material. A variety of catalysts have been developed for the commercial practice of the process and would be known to one skilled in the art. The efficiency of the MEROX process is also a function of the amount of H$_2$S present in the stream. As such, a prewashing step for H$_2$S removal may be included in some refinery processes.

The disulfide oil compounds produced in the MEROX process can contain various disulfides. For example, a MEROX unit designed for the recovery of propane and butane may yield a disulfide oil mixture with the composition set forth in Table 1. The composition of Table 1 is derived from semi-quantitative GC-MS data. The GC-MS results provide evidence for trace quantities of tri-sulfide species; however, the majority of the disulfide oil stream comprises the three components identified in Table 1.

TABLE 1

Disulfide Oil Composition

| Disulfide Oil | Weight Percentage | Boiling Point (BP) | Molecular Weight (MW) | Sulfur Weight Percentage |
|---|---|---|---|---|
| Dimethyldisulfide | 15.7 | 110 | 94 | 68.1 |
| Diethyldisulfide | 33.4 | 152 | 122 | 52.5 |
| Methylethyldisulfide | 49.3 | 121 | 108 | 59.3 |
| Total (Average) | 98.4 | (128) | (109) | (57.5) |

In various embodiments, the hydrocarbon stream containing mercaptans 1 is natural gas, fuel gas, liquefied petroleum gas, a pentane mixture, light straight run naphtha, light thermally cracked naphtha, full straight run naphtha, full FCC cracked naphtha, heavy FCC cracked naphtha, heavy SR naphtha, aviation turbine fuel, kerosene, or a distillate fuel having a boiling point of up to 350° C.

Having briefly described the MEROX process and the resulting DSO by-product stream, the utilization and disposal of the generated DSO by-product stream is explored.

Specifically, the by-product stream comprising the DSO may be processed in a steam cracking unit to produce a DSO free product stream.

An illustrative embodiment of the process and system of the present disclosure will be described with reference to FIGS. 2 and 3 in which the by-product stream 7 of disulfide oil (DSO) compounds from the generalized MEROX unit of FIG. 1 is treated. It will be understood that the processing of the combined propane and butane stream of FIG. 1 is illustrative only and that separate streams of the products, and combined or separate streams of other mixed and longer chain products can be the subject of the present process for removing mercaptans from a hydrocarbon stream containing mercaptans and converting by-product disulfide oil to useful products.

In order to practice the integrated refinery process of the present disclosure as illustrated in conjunction with the MEROX unit operation of FIG. 1, it is necessary to add one or more apparatus to convert the by-product disulfide oil to useful products. Such apparatus, as illustrated in FIGS. 2 and 3, may include the introduction of a steam cracking unit 30 into which the DSO compounds in the by-product stream 7 are introduced for further processing. It will be appreciated that steam cracking is a petrochemical process in which saturated hydrocarbons are broken down into smaller, often unsaturated, hydrocarbons and is one of the principal industrial methods for producing lighter hydrocarbons from various feedstocks. In steam cracking, a gaseous or liquid hydrocarbon feed is diluted with steam and briefly heated in a furnace without the presence of oxygen which cracks the hydrocarbon feed into lighter hydrocarbons. The introduction of such steam cracking unit into the presently disclosed integrated refinery process produces useful products from the generally considered undesirable by-product stream 7 comprising DSO output from the MEROX process. For example, in accordance with the present disclosure, operation of the steam cracking unit 30 may generate a DSO free product stream comprising a light hydrocarbon gases stream 12 including hydrogen sulfide, an aromatic hydrocarbons stream 13 (including benzene, toluene, styrene, xylenes), a pyrolysis gasoline stream 14, a pyrolysis fuel oil stream 15, and a carbon disulfide stream 16 dependent on the composition of the feed to and processing conditions of the steam cracking unit 30. It will be appreciated that the products produced in the reaction present in the steam cracking unit 30 depends on the composition of the feed, the steam to hydrocarbon ratio, and on the cracking temperature and furnace residence time.

Figure 2:
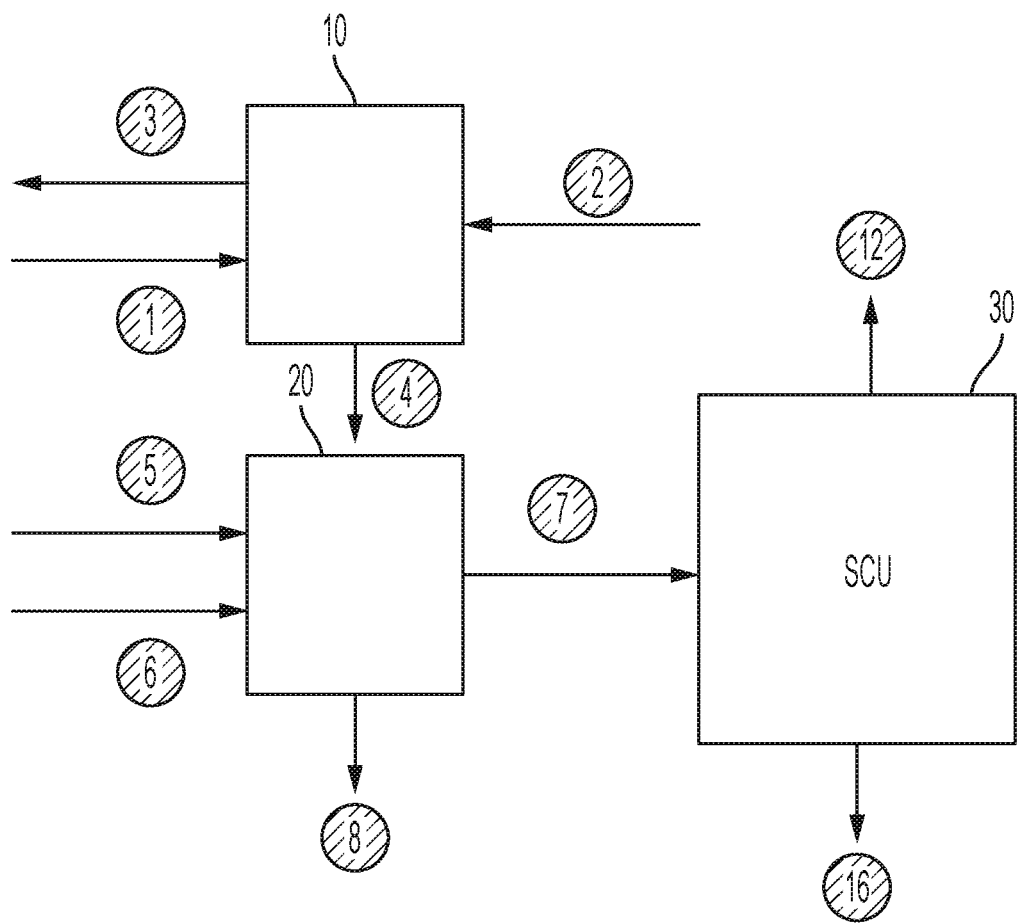
FIG. 2 is a simplified schematic diagram of one or more embodiments of the integrated refinery process of the present disclose.

With reference to FIG. 2, the steam cracking unit 30 is placed in fluid communication with the by-product stream 7 comprising DSO output from the MEROX process. In one or more embodiments, the steam cracking unit 30 may be directly fed by the by-product stream 7, thereby feeding DSO to the steam cracking unit 30. The DSO free product stream generated from the by-product stream 7 through processing in the steam cracking unit 30 may include a mixture of hydrogen sulfide and carbon disulfide. These streams may be provided from the various outputs of the steam cracking unit 30 including the light hydrocarbon gases stream 12 and the carbon disulfide stream 16.

Figure 3:
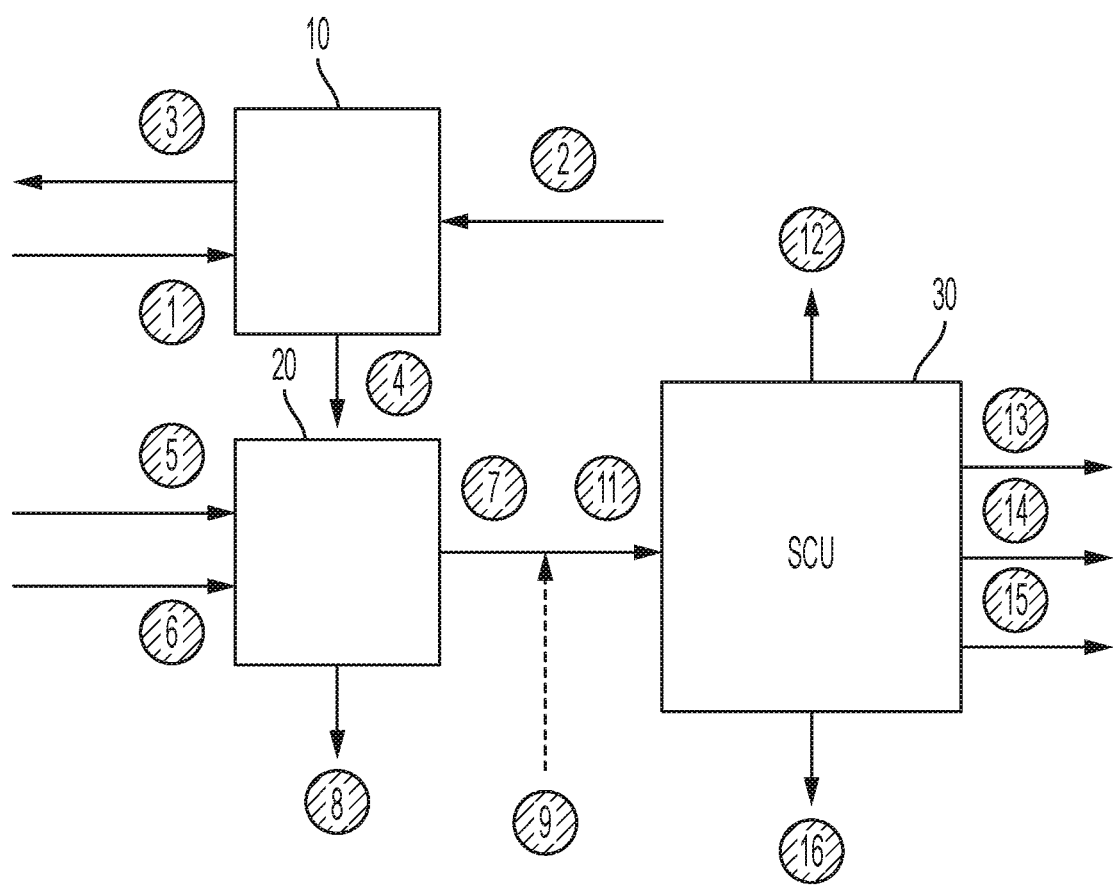
FIG. 3 is a simplified schematic diagram of one or more embodiments of the integrated refinery process of the present disclose.

With reference to FIG. 3, in one or more embodiments, the by-product stream 7 is combined with one or more hydrocarbon streams 9 prior to introduction to the steam cracking unit 30 resulting in a combined hydrocarbon and disulfide oil stream 11 being provided to the steam cracking unit 30 for further processing. The DSO free product stream generated when the feed to the steam cracking unit 30 includes the by-product stream 7 in combination with the one or more hydrocarbon streams 9 may include a mixture of hydrogen sulfide, light gases, benzene, toluene, styrene, xylenes, pyrolysis gasoline, and pyrolysis oil. These streams may be provided from the various outputs of the steam cracking unit 30 including the light hydrocarbon gases stream 12, the aromatic hydrocarbons stream 13 (including benzene, toluene, styrene, xylenes), the pyrolysis gasoline stream 14, and the pyrolysis fuel oil stream 15.

It will be appreciated that the products produced by the steam cracking unit 30 depends on the composition of the feed to the steam cracking unit 30. The one or more hydrocarbon streams 9 which are combined with the by-product stream 7 to form the combined hydrocarbon and disulfide oil stream 11 may include any mercaptan free hydrocarbons. Examples of hydrocarbon stream 9 include one or more of light hydrocarbons such as ethane, propane, butanes; light naphtha paraffinic hydrocarbons containing 5-6 carbons atoms; heavy naphtha hydrocarbons containing paraffins; naphthenes; aromatics with carbons number in the range of 7 to 12; mid distillate hydrocarbons containing paraffins; naphthenes and aromatics with boiling points in the range of 180 to 370° C., and SR or hydrotreated vacuum gas oil with boiling points in the range of 370 to 565° C. In one or more specific embodiments, the one or more hydrocarbon steams 9 may comprise diesel fuel and more specifically ultra-low sulfur diesel fuel having less than 10 parts per million (ppm) sulfur in selected embodiments.

Having described the integrated refinery process in general terms, specific operating parameters for the integrated refinery process in various embodiments will be described. The MEROX process has multiple parameters and inputs which may be adjusted to achieve desirable mercaptans removal from the mercaptan containing hydrocarbon stream 1. Specifically, conversion of the mercaptans to water soluble alkali metal alkylthiolate compounds in the extraction vessel 10 and subjecting the spent caustic from the extraction vessel 10 which contains the alkali metal alkanethiolates to air oxidation to produce the by-product dilsulfide oil stream may each be completed with specific operating parameters.

In one or more embodiments, the conversion of the mercaptans to water soluble alkali metal alkanethiolate compounds in the extraction vessel 10 includes passing the hydrocarbon stream 1 through an extraction section (not shown) of the extraction vessel 10. The extraction section of the extraction vessel 10 includes one or more liquid-liquid contacting decks enabling reaction of the caustic solution 2 and the mercaptans in the hydrocarbon stream 1 and ultimate conversion of the mercaptans to alkali metal alkanethiolates. Such contact at the liquid-liquid contacting decks in the extraction section of the extraction vessel 10 may be completed at a temperature of 15° C. to 80° C. and a pressure of 10 to 50 bars. In various further embodiments, contacting of the caustic solution 2 and the mercaptans in the hydrocarbon stream 1 at the liquid-liquid contacting decks in the extraction section of the extraction vessel 10 may be completed at a temperature of 20° C. to 75° C., 30° C. to 75° C., or 40° C. to 60° C., each at a pressure of 10 to 50 bars.

In one or more embodiments, the caustic solution is circulated at 1 to 3 volume percent (vol. %) for liquid petroleum gas (LPG) as the hydrocarbon stream 1 and 10 to 20 vol. % for a naphtha based hydrocarbon stream 1.

In one or more embodiments, the combined spent caustic and alkali metal alkanethiolate stream 4 exiting the extraction vessel 10 is provided to the wet air oxidation reactor 20 to produce the by-product stream 7 containing disulfide oils (DSO) and sulfides. Within the wet air oxidation reactor 20, the catalyst 5 and air 6 regenerate the spent caustic in the spent caustic and alkali metal alkanethiolate stream 4 as well as convert the alkali metal alkanethiolate compounds to disulfide oils. Such operation may be completed at a temperature of 20° C. to 300° C. In various further embodiments, the regeneration of the spent catalyst and conversation of the alkali metal alkanethiolate compounds to disulfide oils may be completed at a temperature of 20° C. to 150° C., 20° C. to 100° C., or 20° C. to 80° C.

The by-product stream 7 with the DSO is further passed to the steam cracking unit 30 to generate the DSO free product stream of useful products. As previously indicated, the products produced in the reaction present in the steam cracking unit 30 depends on a multitude of factors including the composition of the feed, the steam to hydrocarbon ratio, and on the cracking temperature and furnace residence time.

In one or more embodiments, the steam to hydrocarbon ratio at the steam cracking unit 30 is 0.1:1 to 1:1, that is 0.1 to 1 kilogram (Kg) water per Kg of hydrocarbons. In various further embodiments, the steam to hydrocarbon ratio at the steam cracking unit 30 is 0.2:1 to 1:1, 0.3:1 to 1:1, 0.4:1 to 1:1, 0.5:1 to 1:1, or approximately 0.6:1.

The temperature within the steam cracking unit 30 affects the resultant products. The cracking temperature may also be referred to as the severity. It will be appreciated that generally a greater cracking temperature or severity results in shorter carbon chain products such as ethene and benzene, whereas lesser cracking temperatures or severity generally produces a greater proportion of longer chain hydrocarbons such as propene, C4-hydrocarbons and liquid products. In one or more embodiments, the steam cracking unit 30 is operated at a temperature of 800° C. to 850° C. In various further embodiments, the operating temperature of the steam cracking unit 30 may be 800° C. to 950° C., 800° C. to 900° C., or 850° C. to 900° C.

In various embodiments, the steam cracking unit 30 is operated at a pressure of 1 to 10 bars, 1 to 5 bars, 1 to 2 bars, or approximately 1.5 bars.

In various embodiments, the steam cracking unit 30 is operated with a residence time of the by-product steam in the steam cracking unit of 0.1 to 1.5 seconds, 0.5 to 1.5 seconds, 0.3 to 1.0 seconds, or approximately 0.7 seconds.

Inclusion of DSO with a hydrocarbon feed unexpectantly improves yield of higher value C8 aromatics upon steam cracking of the hydrocarbon feed. Specifically, the addition of DSO to a hydrocarbon feed generates more xylene products than the hydrocarbons stream alone processed in a steam cracking unit.

In one or more embodiments, the DSO free product stream generated as the products stream from the steam cracking unit 30 comprises an increased mass percentage of higher value C8 aromatics. Alternatively or additionally, inclusion of DSO in the feed stream to the steam cracking unit 30 results in at least an increase in 1 percent by weight of C8 aromatics in the resultant DSO free product stream.

Without wishing to be bound by theory, it is believed that the DSO serves as a co-catalyst to boost xylene yield. Such observation and conclusion may be made based on the increased xylene yield.

EXAMPLES

The following examples illustrate features of the present disclosure but are not intended to limit the scope of the disclosure.

To demonstrate the utility of utilization of the by-products stream comprising DSO from a MEROX process to generate useful products and alleviate the disposal environmental disposal burden, pilot plant testing was completed. Specifically, disulfide oil samples representing the by-products stream of the MEROX process were processed in a steam cracking unit consistent with embodiments of the present disclosure. Testing was completed for both neat DSO samples in accordance with the by-product stream 7 of FIG. 2 as well as for streams comprising the DSO as well as additional hydrocarbons in accordance with the combined hydrocarbon and disulfide oil stream 11 of FIG. 3.

Inventive Example 1

A disulfide oil sample with a composition in accordance with Table 1 was dissolved in water to its solubility limit to prepare test solution A. Test solution A was then subjected to steam cracking at a coil outlet temperature of 800° C. and 1.5 bars of pressure. The residence time of test solution A within the steam cracking unit was 0.7 second. The effluent from the steam cracking unit was collected and analyzed to determine the make-up of the resulting DSO free product stream. The compositional make-up of the DSO free product stream from steam cracking of test solution A at 800° C. and 1.5 bars of pressure with a residence time of 0.7 second is provided in Table 2.

TABLE 2

| Inventive Example 1 - Product Composition | |
|---|---|
| Component | Weight Percentage |
| hydrogen sulfide ($H_2S$) | 75.7 |
| Carbon disulfide ($CS_2$) | 24.3 |

The composition of the DSO free product stream from steam cracking of test solution A was determined using gas chromatography. Specifically, characterization of the reactor effluent was performed with two separate gas chromatographs. A refinery gas analyzer (RGA) which is calibrated to 19 compounds in the C1-C4 range and a comprehensive two-dimensional gas chromatograph coupled to a flame ionization detector (FIDA as well as to a sulfur chemiluminescence detector (SCD) for sulfur detection were utilized. For the analysis of sulfur compounds a SCD coupled to a comprehensive GC×GC was used. For this, a premixed standard mixture, with a defined concentration of 3-chlorothiophene ($C_4H_3ClS$) diluted in hexane, was fed to the downstream section of the reactor.

Inventive Example 2

To demonstrate the effect of processing temperature on the DSO free product stream exhausted from the steam cracking unit, a disulfide oil sample with a composition in accordance with Table 1 was once dissolved in water to its solubility limit to prepare additional test solution A. Test solution A was then subjected to steam cracking at a coil outlet temperature of 850° C. (in comparison to 800° C. of Inventive Example 1) and 1.5 bars of pressure. The residence time of test solution A within the steam cracking unit was 0.7 second. The effluent from the steam cracking unit was collected and analyzed to determine the make-up of the resulting DSO free product stream. The compositional make-up of the DSO free product stream from steam cracking of test solution A at 850° C. and 1.5 bars of pressure with a residence time of 0.7 second is provided in Table 3. As with Inventive Example 1, the composition of the DSO free product stream from steam cracking of test solution A was determined using gas chromatography.

TABLE 3

Inventive Example 2 - Product Composition

| Component | Weight Percentage |
|---|---|
| hydrogen sulfide ($H_2S$) | 80.9 |
| Carbon disulfide ($CS_2$) | 19.1 |

Inventive Example 3

The production of useful products when DSO is combined with additional hydrocarbons prior to processing in a steam cracking unit was also demonstrated. A disulfide oil sample with a composition in accordance with Table 1 was dissolved in ultra-low sulfur diesel as a representative hydrocarbon stream to form test solution B. The disulfide oil was dissolved in the ultra-low sulfur diesel at 180 to 216 ppm. The specific composition of the ultra-low sulfur diesel utilized is detailed in Table 4. Test solution B was then subjected to steam cracking at a coil outlet temperature of 850° C. and 1.5 bars of pressure. The residence time of test solution B within the steam cracking unit was 0.7 second. The effluent from the steam cracking unit was collected and analyzed to determine the make-up of the resulting DSO free product stream. The compositional make-up of the DSO free product stream from steam cracking of test solution B at 850° C. and 1.5 bars of pressure with a residence time of 0.7 second is provided in Table 5. As with the previous Examples, the composition of the DSO free product stream from steam cracking of test solution B and the specific composition of the ultra-low sulfur diesel was determined using gas chromatography.

TABLE 4

Ultra-low sulfur diesel composition

| Component | Unit | Value |
|---|---|---|
| Sulfur | ppm by weight | 10 |
| Paraffins | w. % | 32.41 |
| Iso-paraffins | w. % | 31.56 |
| Mono-naphthenes | w. % | 16.14 |
| Mono-aromatics | w. % | 15.02 |
| Naphthenes | w. % | 1.74 |
| Di-aromatics | w. % | 3.13 |
| Total | w. % | 100.00 |

TABLE 5

Inventive Example 3 - Product Composition

| Component | Weight Percentage |
|---|---|
| Hydrogen ($H_2$) | 0.82 |
| Methane ($CH_4$) | 13.70 |
| Carbon Monoxide (CO) | 0.36 |
| Ethylene ($C_2H_4$) | 26.42 |
| Propene ($C_3H_6$) | 11.44 |
| 1-Butene (1-$C_4H_8$) | 0.57 |
| Butadiene (1,3-$C_4H_6$) | 3.77 |
| Other C1-C4s | 6.47 |
| Pyrolysis Gas (C5-C9) | 25.07 |
| Pyrolysis Fuel Oil (C10+) | 11.38 |
| Total | 100.00 |

Further, a detailed breakdown of benzene, toluene, styrene, and xylenes in the DSO free product stream is provided in Table 6.

TABLE 6

Inventive Example 3 - Aromatic Composition

| Component | Weight Percentage |
|---|---|
| Benzene | 8.12 |
| Toluene | 4.36 |
| Styrene | 2.81 |
| Xylenes | 2.21 |
| Total | 17.50 |

Comparative Example 4

The improved C8 aromatics production within the useful products when DSO is combined with additional hydrocarbons prior to processing in a steam cracking unit was also demonstrated. The ultra-low sulfur diesel utilized in Inventive Example 3 as detailed in Table 4 was processed without the DSO to provide a baseline measurement. The neat ultra-low sulfur diesel fuel was subjected to steam cracking at a coil outlet temperature of 850° C. and 1.5 bars of pressure. The residence time of the neat ultra-low sulfur diesel within the steam cracking unit was 0.7 second. The effluent from the steam cracking unit was collected and analyzed to determine the make-up of the resulting product stream. The compositional make-up of the product stream from steam cracking of neat ultra-low sulfur diesel at 850° C. and 1.5 bars of pressure with a residence time of 0.7 second is provided in Table 7. As with the previous Examples, the composition of the effluent stream from steam cracking of ultra-low sulfur diesel utilized in Inventive Example 3 was determined using gas chromatography.

TABLE 7

Comparative Example 4 - Product Composition

| Component | Weight Percentage |
|---|---|
| Hydrogen ($H_2$) | 0.77 |
| Methane ($CH_4$) | 12.96 |
| Carbon Monoxide (CO) | 0.15 |
| Ethylene ($C_2H_4$) | 26.98 |
| Propene ($C_3H_6$) | 12.02 |
| 1-Butene (1-$C_4H_8$) | 1.48 |
| Butadiene (1,3-$C_4H_6$) | 4.00 |
| Other C1-C4s | 6.26 |
| Pyrolysis Gas (C5-C9) | 23.78 |
| Pyrolysis Fuel Oil (C10+) | 11.60 |
| Total | 100.00 |

Further, a detailed breakdown of benzene, toluene, styrene, and xylenes in the product stream from Comparative Example 4 is provided in Table 8.

TABLE 8

Comparative Example 4 - Aromatic Composition

| Component | Weight Percentage |
|---|---|
| Benzene | 10.65 |
| Toluene | 4.28 |
| Styrene | 1.30 |
| Xylenes | 1.71 |
| Total | 17.94 |

A comparison of Table 6 and Table 8 makes clear the increase in higher value C8 aromatics when DSO is included with a hydrocarbon feed stream to a steam cracking unit. Such improvement is unexpected and provides the additional benefit of generating a productive and useful use for the by-product stream generated in the MEROX process to remove mercaptan from hydrocarbons. Specifically, neat ultra-low sulfur diesel generated 1.71 w. % xylenes and 3.01 w. % C8 aromatics, but inclusion of DSO increased such yield to 2.21 w. % xylenes and 5.02 w. % C8 aromatics, a 30% and 66% increase, respectively. The increased yield of desirable C8 aromatics represents a dramatic increase when accounting for the total volume of xylene products generated on an annual basis.

It should now be understood the various aspects of the integrated refinery process for removing mercaptans from a hydrocarbon stream containing mercaptans and converting by-product disulfide oil to useful products are described and such aspects may be utilized in conjunction with various other aspects.

According to a first aspect, an integrated refinery process for removing mercaptans from a hydrocarbon stream containing mercaptans and converting by-product disulfide oil to useful products includes (i) introducing the hydrocarbon stream containing mercaptans into an extraction vessel containing an alkaline solution and (ii) passing the hydrocarbon stream through an extraction section of the extraction vessel which includes one or more liquid-liquid contacting decks for reaction to convert the mercaptans to alkali metal alkanethiolates. The process further includes (iii) withdrawing a hydrocarbon product stream free of mercaptans from the extraction vessel and (iv) recovering spent caustic containing alkali metal alkanethiolates from the extraction vessel. The process additionally includes (v) subjecting the spent caustic containing alkali metal alkanethiolates to air oxidation to produce a by-product stream containing disulfide oils (DSO) and sulfides and (vi) processing the by-product stream in a steam cracking unit to produce a DSO free product stream.

A second aspect includes the process of the first aspect in which the DSO free product stream comprises a mixture of hydrogen sulfide and carbon disulfide.

A third aspect includes the process of the first aspect in which the by-product stream is combined with one or more hydrocarbon streams prior to introduction to the steam cracking unit.

A fourth aspect includes the process of the third aspect in which the DSO free product stream comprises a mixture of hydrogen sulfide, light gases, benzene, toluene, styrene, xylenes, pyrolysis gasoline, and pyrolysis oil.

A fifth aspect includes the process of the third or fourth aspects in which the one or more hydrocarbon streams comprise hydrocarbons with a carbon number in the range of 2 to 20.

A sixth aspect includes the process of the third or fourth aspects in which the one or more hydrocarbon streams comprise diesel fuel.

A seventh aspect includes the process of any of the first through sixth aspects in which step (ii) is completed at a temperature of 15° C. to 80° C.

An eighth aspect includes the process of any of the first through seventh aspects in which step (ii) is completed at a pressure of 10 to 50 bars.

A ninth aspect includes the process of any of the first through eighth aspects in which step (v) is completed at a temperature of 20° C. to 300° C.

A tenth aspect includes the process of any of the first through ninth aspects in which step (vi) is completed at a temperature of 800° C. to 850° C.

An eleventh aspect includes the process of any of the first through tenth aspects in which step (vi) is completed at a steam to hydrocarbon ratio of 0.1:1 to 1:1.

A twelfth aspect includes the process of any of the first through tenth aspects in which step (vi) is completed at a steam to hydrocarbon ratio of 0.5:1 to 1:1.

A thirteenth aspect includes the process of any of the first through twelfth aspects in which step (vi) comprises a residence time of the by-product steam in the steam cracking unit of 0.1 to 1.5 seconds.

A fourteenth aspect includes the process of any of the first through thirteenth aspects in which the hydrocarbon stream containing mercaptans is natural gas, fuel gas, liquefied petroleum gas, a pentane mixture, light straight run naphtha, light thermally cracked naphtha, full straight run naphtha, full FCC cracked naphtha, heavy FCC cracked naphtha, heavy SR naphtha, aviation turbine fuel, kerosene, or a distillate fuel having a boiling point of up to 350° C.

A fifteenth aspect includes the process of any of the first through fourteenth aspects in which the by-product stream comprises a minor proportion of sulfides and a major proportion of disulfide oils.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned. For brevity, the same is not explicitly indicated subsequent to each disclosed range and the present general indication is provided.

As used in this disclosure and in the appended claims, the words "comprise," "has," and "include" and all grammatical variations thereof are each intended to have an open, non-limiting meaning that does not exclude additional elements or steps.

What is claimed is:

1. An integrated refinery process for removing mercaptans from a hydrocarbon stream containing mercaptans and converting by-product disulfide oil to useful products, the process comprising:
   (i) introducing the hydrocarbon stream containing mercaptans into an extraction vessel containing an alkaline solution;
   (ii) passing the hydrocarbon stream through an extraction section of the extraction vessel which includes one or more liquid-liquid contacting decks for reaction to convert the mercaptans to alkali metal alkanethiolates;
   (iii) withdrawing a hydrocarbon product stream free of mercaptans from the extraction vessel;
   (iv) recovering spent caustic containing alkali metal alkanethiolates from the extraction vessel;
   (v) subjecting the spent caustic containing alkali metal alkanethiolates to air oxidation to produce a by-product stream containing disulfide oils (DSO) and sulfides, wherein the DSO comprises dimethyldisulfide, diethyldisulfide, and methylethyldisulfide; and
   (vi) feeding the by-product stream directly to a steam cracking unit without dilution, and processing the by-product stream in the steam cracking unit to produce a DSO free product stream.

2. The process of claim 1 in which the DSO free product stream comprises a mixture of hydrogen sulfide and carbon disulfide.

3. The process of claim 1 in which step (ii) is completed at a temperature of 15° C. to 80° C.

4. The process of claim 1 in which step (ii) is completed at a pressure of 10 to 50 bars.

5. The process of claim 1 in which step (v) is completed at a temperature of 20° C. to 300° C.

6. The process of claim 1 in which step (vi) is completed at a temperature of 800° C. to 850° C.

7. The process of claim 1 in which step (vi) comprises a residence time of the by-product steam in the steam cracking unit of 0.1 to 1.5 seconds.

8. The process of claim 1 in which the hydrocarbon stream containing mercaptans is natural gas, fuel gas, liquefied petroleum gas, a pentane mixture, light straight run naphtha, light thermally cracked naphtha, full straight run naphtha, full FCC cracked naphtha, heavy FCC cracked naphtha, heavy SR naphtha, aviation turbine fuel, kerosene, or a distillate fuel having a boiling point of up to 350° C.

9. The process of claim 1 in which the by-product stream comprises a minor proportion of sulfides and a major proportion of disulfide oils.

* * * * *